United States Patent [19]

Ohmori et al.

[11] Patent Number: 5,431,925
[45] Date of Patent: Jul. 11, 1995

[54] NUTRITIVE COMPOSITION FOR PREVENTION AND THERAPY OF INFECTION DISEASES CAUSED BY IMMUNOSUPPRESSION

[75] Inventors: Toshihiro Ohmori; Minoru Yanai, both of Tochigi, Japan

[73] Assignee: Snow Brand Milk Products Co., Ltd., Hokkaido, Japan

[21] Appl. No.: 184,921

[22] Filed: Jan. 24, 1994

Related U.S. Application Data

[62] Division of Ser. No. 988,680, Dec. 10, 1992, abandoned.

[30] Foreign Application Priority Data

Dec. 13, 1991 [JP] Japan .................................. 3-51295

[51] Int. Cl.$^6$ ...................... A61K 33/26; A61K 37/00; A61K 31/70; A61K 31/715
[52] U.S. Cl. ........................................ 424/646; 514/2; 514/23; 514/52; 514/53; 514/54; 514/58; 514/168; 514/249; 514/251; 514/276; 514/345; 514/355; 514/458; 514/474; 514/725

[58] Field of Search ..................... 424/195.1, 523, 646; 514/2, 23, 53, 54, 58, 60, 549, 552, 561, 725, 532, 52, 249, 168, 251, 276, 345, 355, 458, 474, 547

[56] References Cited

U.S. PATENT DOCUMENTS

| | | | |
|---|---|---|---|
| 4,752,618 | 6/1988 | Mascioli et al. | 514/549 |
| 4,981,844 | 1/1991 | Alexander et al. | 514/21 |

*Primary Examiner*—Raymond Henley, III
*Attorney, Agent, or Firm*—Burgess, Ryan & Wayne

[57] ABSTRACT

Disclosed is a nutritive composition for patients being treated with anticancer drugs, which comprises 1-5 mg weight % of a retinoid compound in the solid content of the composition composed of proteins, carbohydrates, fats, vitamins and minerals as major components. It can prevent the immunosuppression induced by the administration of anticancer drugs, and can prevent the infectious diseases arising from said immunosuppression and helps to enhance the therapeutic effect on the patients.

7 Claims, 1 Drawing Sheet

NUTRITIVE COMPOSITION FOR PREVENTION AND THERAPY OF INFECTION DISEASES CAUSED BY IMMUNOSUPPRESSION

This is a division, of application Ser. No. 07/988,680, filed Dec. 10, 1992, now abandoned.

BACKGROUND OF THE INVENTION

1. Field of the Invention

The present invention relates to a nutritive composition useful for preventing infectious diseases. The nutritive composition of the present invention is effective for the prevention and therapy of infectious diseases due to immunosuppression induced by administration of anticancer drugs.

2. Description of the Background Art in recent years, important relationships between nutrition and diseases have become clear; in particular, the relationship between immunity and nutrition is considered to be of primary importance. The normal immune response by a living body is depressed with a decline in nutrition, resulting in induction of bacterial infection diseases and the like. In this regard, active feeding of a high-energy nutrition is widely practiced in the patients who suffered from excessive burden such as surgical operation or the like, for the purpose of accelerating restoration or preventing the immunosuppression induced by such operation. High-energy transfusions, enteral feedings, and the like have been developed as such nutritive feedings. By these feedings, immunosuppression arising from malnutrition can be prevented to a large extent. On the other hand, infectious diseases arising from immunosuppression which is induced by other diseases or medical treatments are experienced frequently. Specifically, marked depression of immune response is often observed in the patients who have cancer. Such immunosuppression is evidently caused by malnutrition as a result of anorexia, immunosuppresants produced by neoplasm histoma, or by being exposed to radiation or administration of anticancer drugs for the treatment of cancer. In the therapy for cancer, therefore, immunotherapeutic drugs such as Krestin, Picibanil, interferon, G-CSF, and the like, are administered to the patients in addition to nutritional care. Nevertheless, administration of these drugs does not bring about appreciable effects on the immunosuppression induced by cancer treatments, especially it is not effective for the therapy of infectious diseases. Furthermore, it is known that administration of anticancer drugs suppresses the marrow function which involves the production of immunocytes, and, at the same time, injures gastromucos membranes, inducing conditions where the patients are susceptible to infectious diseases. Due to these causes and reasons, endogenous infection diseases are included by administration of anticancer drugs.

SUMMARY OF THE INVENTION

In view of this situation the present inventors have undertaken extensive studies on the mechanisms of immunosuppression and occurrence of infectious diseases induced by administration of anticancer drugs, and have found that these diseases can be prevented and treated by a nutritional control.

Therefore, an object of the present invention is to provide a nutritive preparation which has functions of preventing and curing the immunosuppression and subsequent infectious diseases induced by administration of anticancer drugs.

According to the present invention a nutritive composition is provided, which is capable of feeding a high-energy. nutrition and has preventive and therapeutic effects on bacterial infection diseases, while improving the depressed immune response induced in patients by the administration of anticancer drugs.

The above object can be achieved according to the present invention by providing a nutritive composition having an activity of improving immunosuppression induced by administration of anticancer drugs and comprising a nutritive preparation comprising protein, carbohydrate, lipid, vitamin, and mineral, as major components, and further comprising 1–5 mg % by weight, based on the solid weight of said composition, of a retinoid compound.

Other objects, features and advantages of the invention will hereinafter become more readily apparent from the following description.

DETAILED DESCRIPTION OF THE INVENTION AND PREFERRED EMBODIMENTS

Figure 1:
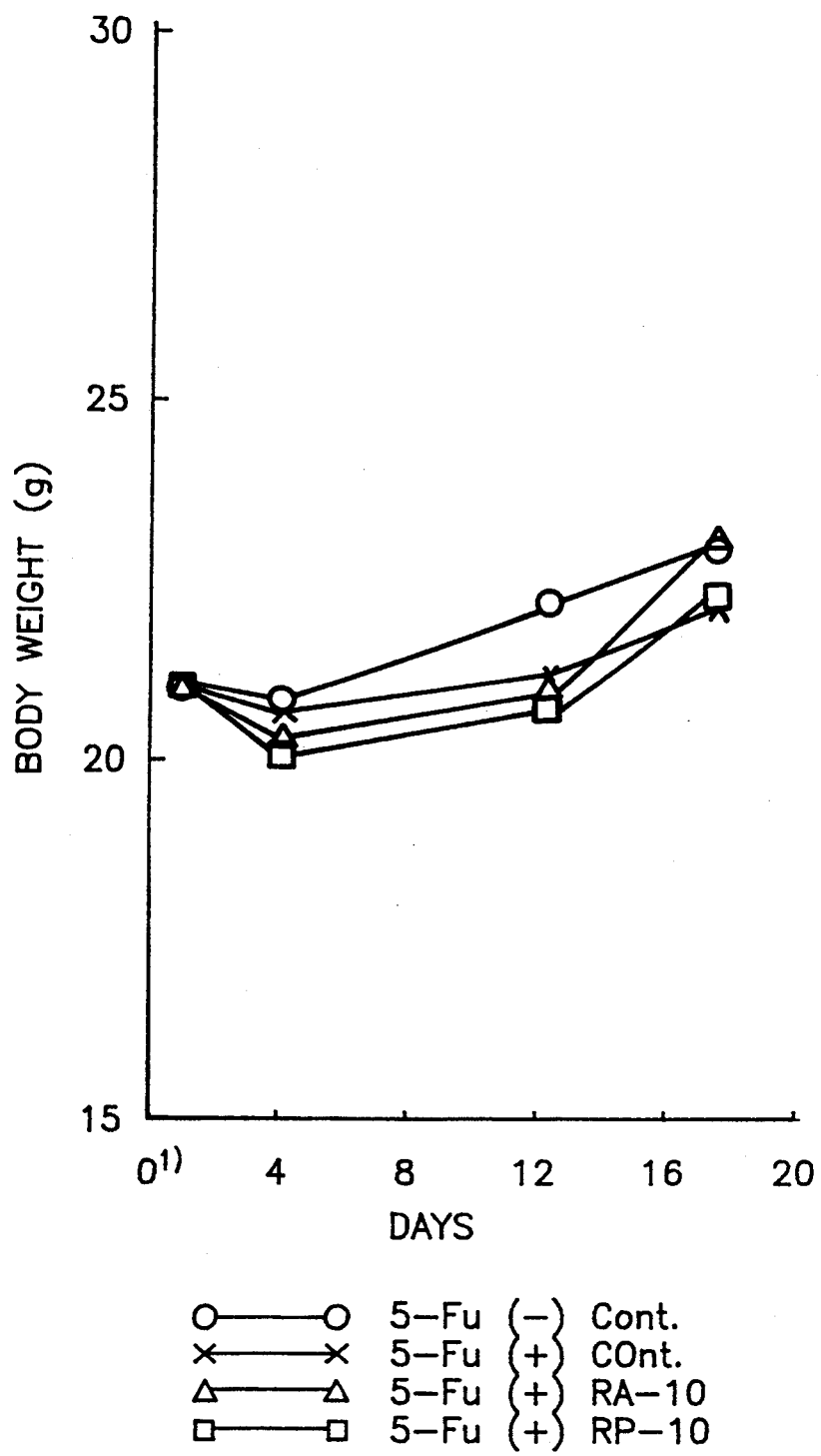
FIG. 1 shows the body weight changes in rats to which the nutritive preparation of the present invention was administered.

Recently, it has been revealed that nutritive ingredients serve not only as essential components for retention of functions and growth of living body but also have various pharmacological effects such as curing of specific diseases. Various foods containing such nutritive ingredients which exhibit said pharmacological effects have attracted attention as physiologically functional foods. The nutritive preparation of the present invention provides both the immunoreactivity effect due to retinoid compounds known as vitamin A and the nutritional effects of such ingredients as proteins, lipids, carbohydrates, vitamins, minerals, and the like. In particular, according to the nutritive preparation composition of the present invention, the toxicity problems pertaining to the retinoid compounds can be suppressed.

Vitamin A is separated from liver oil as an effective ingredient for bed-wetting and exists as in various forms as derivatives. Vitamin A and these derivatives are called collectively as "retinoid compounds." Vitamin A is defined by the international unit (IU) as 1 IU=0.3 $\mu$g of retinoid, a kind of retinoid compound. Retinoid compounds have an anticancer activity; in particular, retinoic acid has a strong effect against skin cancer and the like, but is not used for actual clinic treatment because of its strong toxicity. Massive intake of these retinoid compounds causes brain hypertension, hepatic disorder, and the like. The daily intake of vitamin A, therefore, is limited to 2,000 IU (0.6 mg as retinol) for adult male and 1,800 IU (0.54 mg as retinol) for adult female. The toxicity of retinoid compounds expressed as $LD_{50}$ (mouse) is 4,100 mg/kg or higher for retinol and 4,000 mg/kg or higher for retinoic acid.

Retinoid compounds are added to foods in which the effect as vitamin A is desired. A wide variety of such commercial products are available as physiological nutrients, in which it is indicated that 500–1,000 IU of vitamin A for 100 g is contained. This content is equivalent to only 0.15–0.3 mg of retinol, which is apparently insufficient in the light of our finding, i.e. for the purpose of prevention of immunity depression or prevention and therapy of resulting infectious diseases. It is essentially necessary that in a nutritive preparation comprising proteins, carbohydrates, lipids, vitamins, and minerals, as major components, the content of retinoid compounds must be 1–5 mg % by weight or more of the solid content of the nutrient. The content of retinoid compounds is preferably less than 10 mg/100 g, because side-effect problems arise when it exceeds 10 mg/100 g. When the nutritive preparation is designed to contain more than 10 mg of retinoid compounds, it is necessary to adjust the total daily intake of retinoid compounds by decreasing other foods to be taken.

The restoration of immunological competence can be expected by feeding of a nutritive preparation in which a required amount of retinoid compounds is incorporated into a conventional nutritive composition comprising proteins, lipids, carbohydrates, vitamins, and minerals as major components. The toxicity of retinoid compounds, which arises when retinoid compounds are administered individually, can also be suppressed by the composition of the present invention.

The retinoid compounds to be used in the present invention may be various compounds known as vitamin A, including retinol, retinal, retinoic acid, 3-dehydroretinol, 3-dehydroretinal, 3-dehydroretinoic acid, and esters and derivatives thereof. Any other compounds generally known as a retinoid can also be used in addition to those herein specifically described.

Proteins to be used in the present invention are those easily digestible and highly nutritious; for example, egg proteins, milk proteins, soybean proteins, fish proteins, meat proteins, and their enzymatic hydrolysates, peptide mixtures, amino acid mixtures, and the like. It is very important to select easily digestible proteins, because the subjects to which the composition of the present invention is given are the patients whose digestion and absorption abilities are depressed by medication of anticancer drugs. From this aspect, amino acid mixtures, peptide mixtures, enzymatic hydrolysates, and the like, are preferable.

As lipids, animal or vegetable oils are incorporated to supply essential fatty acids and high energy. The use of lipids composed of medium chain triglyceride (MCT) or the like, which are to be absorbed without being converted to chylomicrons, can help to supply high calorie easily to the patients whose digestive and absorptive abilities are depressed. For the supply of essential fatty acids, soybean oil, corn oil, safflower oil, and the like may be used. Also, fish oil or milk fat, or mixtures of these fat and oil can be used.

The carbohydrates to be used in the present invention are starch, dextrin, and their hydrolysates. Monosaccharides, e.g., glucose, fructose, etc., and disaccharides, e.g., sucrose, lactose, maltose, etc., can also be used.

The contents of proteins, lipids and carbohydrates in the nutritive preparation of the present invention are 10–40% by weight of proteins, 5–30% by weight of lipids, and 50–80% by weight of carbohydrates, based on the total solid components. The content of lipids is desirably less than 30% by weight for the patients whose digestive and absorptive abilities are depressed due to the administration of anticancer drugs. However, it is possible to increase the content of lipids by adopting specific lipids such as medium chain triglyceride (MCT) and the like.

Vitamins other than vitamin A are added to satisfy the essential requirement as trace elements. Other essential ingredients necessary for the nutrition are further added in the form of salts, though essential trace elements and minerals may be entrained with aforementioned components. Emulsifiers and stabilizers can optionally be added to retain the emulsification stability of the nutritive composition.

Dietary fibers such as microcrystalline cellulose, mannan, pectin, and the like can be further added to the nutritive composition of the present invention, as required. These dietary fibers are expected to stimulate the digestive tract canal, activate the digestive and absorptive activities, and prevent constipation.

The nutritive composition of the present invention can be prepared in liquid form by dissolving and mixing the raw materials, followed by pasteurization and homogenization. Also, powdery products can be prepared by spray drying or lyophilization after the raw materials have been homogenized. The powdery products are administered to patients after dissolved in water or hot water at a solid concentration of 15–25%.

The nutritive composition of the present invention is administered usually in a sufficient amount to provide amount 200–500 g (containing 10–30 mg retinoid) as nutritious foods.

By the administration of a nutritive composition of the present invention to the patients whose immune response have been depressed on account of intake of anticancer drugs, improvement in the nutritional conditions, as well as prevention and cure of the immunosuppression and subsequent infectious diseases can be achieved.

Other features of the invention will become apparent in the course of the following description of the exemplary embodiments which are given for illustration of the invention and are not intended to be limiting thereof.

EXAMPLES

EXAMPLE 1

To 62 kg of milk casein, 1.3 kg of sodium carbonate to dissolve the milk casein, 273 kg of powdery starch sugar, 61 kg of medium chain triglyceride, 19 kg of corn oil 13 g of vitamin D oil (500,000 IU/g), 5.2 g of retinoic acid or retinol palmitate, 15 g of vitamin E, and 584 kg of water were added to prepare 1,000 kg of a mixed solution. The solid content of this mixture was 40% by weight. 320 kg of crude powder was prepared from this mixture by pasteurizing and homogenizing, followed by spray drying. 65 kg of this crude powder was mixed with 28 kg of skim milk powder in which lactose has been decomposed to the extent of 75% by enzymatic hydrolysis, 6 kg of whole milk powder, 150 g of L-methionine, 60 g of L-tryptophan, 140 g of calcium carbonate, 50 g of sodium iron citric acid succinate, 0.5 g of vitamin B1, 1 g of vitamin B6, 10.2 g of vitamin C, 4.5 g of nicotinic acid amide, 3.4 g of calcium pantothenate, 90 mg of folic acid to prepare a product. The analytical data of this product are given in Table 1. The product was dissolved in 340 ml of sterilized distilled water. 400 g of this solution was divided into several doses and administered to cancer patients several times a day orally or as a per enteral nutrition.

TABLE 1

| Components | Nutrition Analysis Analytical Value |
|---|---|
| Protein | 20 g |

TABLE 1-continued

| Nutrition Analysis | |
|---|---|
| Components | Analytical Value |
| Lipid | 15 g |
| Carbohydrate | 59 g |
| Ash | 3.2 g |
| Calcium | 440 mg |
| Iron | 5 mg |
| Vitamin C | 10.2 mg |
| Vitamin B1 | 0.5 mg |
| Vitamin B2 | 0.8 mg |
| Vitamin B6 | 1.0 mg |
| Vitamin B12 | 0.68 mg |
| Vitamin D | 100 IU |
| Vitamin E | 3.4 IU |
| Nicotinic acid amide | 4.5 mg |
| Calcium pantothenate | 3.4 mg |
| Folic acid | 90 μg |
| Retinoic acid or Retinol palmitate | 5 mg |

EXAMPLE 2

A nutritive composition of the formulation of Table 2 was prepared in the same manner as in Example 1. The content of retinoic acid or retinol palmitate was adjusted to 1 mg or 5 mg per 100 g of final products.

TABLE 2

| Formulation | |
|---|---|
| Raw materials | Content (%) |
| Corn starch | 45.5 |
| Casein | 24.5 |
| Sucrose | 10.0 |
| Microcrystalline cellulose | 5.0 |
| MCT | 3.0 |
| Safflower oil | 3.0 |
| α-Starch | 1.0 |
| Mixture of minerals | 7.0 |
| Mixture of vitamins | 1.0 |

Analytical values of the nutritive composition per 100 g of the product are given in Table 3.

TABLE 3

| Nutrition Analysis | |
|---|---|
| Components | Analytical Value |
| Protein | 24.5 g |
| Lipid | 6 g |
| Carbohydrate | 61.6 g |
| Ash | 4.2 g |
| Calcium | 891 mg |
| Iron | 4 mg |
| Vitamin C | 18 mg |
| Vitamin B1 | 1.5 mg |
| Vitamin B2 | 1.5 mg |
| Vitamin B6 | 1.0 mg |
| Vitamin B12 | 50 μg |
| Vitamin D | 100 IU |
| Vitamin E | 3.0 IU |
| Vitamin K | 0.2 mg |
| Biotin | 10 μg |
| Inositol | 15 mg |
| Choline chloride | 300 mg |
| Calcium pantothenate | 2.0 mg |
| Folic acid | 0.1 mg |
| Retinoic acid or Retinol palmitate | 1 mg or 5 mg |

EXPERIMENTAL EXAMPLES

In these experiments, the preventive effect on immunosuppression and the preventive and therapeutic effects for infectious disease in mice whose immune response have been depressed by the administration of cancer drug 5-FU, were confirmed using the nutritive composition prepared in Example 2. Retinol acetate was selected as the retinoid compound for the control group by adjusting its retinoid content to 0.4 mg/100 g, and two different contents (1 mg or 5 mg) were prepared for the test groups adopting two other kinds of retinoid, i.e. retinoic acid and retinol palmitate. The test groups to which 1 mg of retinoic acid or 5 mg of retinoic acid was administered were respectively designated as RA-10 and RA-50; while the groups to which 1 mg of retinol palmitate or 5 mg of retinol palmitate was administered were designated RP-10 and RP-50, respectively.

1) Animal used for the experiment

C3H/He mice of 7 week age (female, body weight 20±1 g) were used for the test after preparatory breeding. The models of immunosuppression were prepared by the intraperitoneal injection of 5-FU (manufactured by Kyowa Hakko Kogyo Co., Ltd.) every other day five times at a dose of 25 mg/kg.

2) Administration of the nutritive composition

The feeding of the test food to the mice started on the same day when 5-FU was first administered. The test food was prepared by adding 1% of cellulose and allowed with ad libitum. Each group consisted of 36 mice, and on the 10th day, seven of them were subjected to anatomy for measuring the weight of organs, another seven were subjected to the measurement of delayed-type hypersensitivity reaction (DTH) and remaining 15 were used for the infection experiments.

3) Effect on the body weight

The body weights of mice decreased along with the administration of 5-FU, but recovered quickly to the same level as the body weights of the group to which no 5-FU was administered along with the medication of the nutritive composition of the present invention. FIG. 1 shows changes in the body weight of the groups to which 10 mg of retinoic acid or 10 mg of retinol palmitate was administered. It was confirmed that the nutritive composition of the present invention could restore the body weight decrease by 5-FU intake. Furthermore, any detrimental effects with single and massive administration of retinoid compounds were not observed. These effects are considered to be attributable to the administration of the nutritive composition of the present invention.

4) Effects on the number of leukocytes, bone marrow cells, peritoneal exudate cells.

Antitumor drugs, such as 5-FU or the like, greatly suppress bone marrow cells or the like which are involved in immune response. The effects of the nutritive composition on the numbers of leukocytes, bone marrow cells, peritoneal exudate cells, were examined on the 10th day alter the administration of retinoid. The number of leukocytes were measured by collecting blood from orbital venous plexus posterior into a tube filled with EDTA using an automatic multicytometer E-4000 (trade mark, a product of Toa Medical Electronic Co.). Bone marrow cell samples to be counted were prepared from a hind leg of dehematized and slaughtered mice, by squeezing out the bone marrow fluid by a cold Hanks' solution using a glass syringe with a tuberculin needle. The solution containing the collected bone marrow cells was centrifuged for 5 minutes at 3000 rpm. The bone marrow cells thus prepared was treated with a Tris-HCl buffer to destroy the erythrocytes in the bone marrow cells and to adjust its volume to a prescribed amount with the Hanks' solution.

Then the number of bone marrow cells were counted using a hemacytometer. The number of peritoneal exudate cells were measured by preparing the sample as follows. Five (5) ml of a cold Hanks' solution was injected into the peritoneal cavity of dehematized and slaughtered mouse and collected after giving massage to the peritoneum. Peritoneal exudate cells were collected by washing the inside of the peritoneal cavity three times using the Hanks' solution. These solutions were, after adjusting their volumes, subjected to the measurement of peritoneal exudate cells by a cytometer. The results are shown in Table 4.

TABLE 4

Effects on the numbers of leukocytes, bone marrow cells, peritoneal exudate cells on the 10th day after the administration of retinoid

| Feeding | 5-FU | number of leukocytes × $10^2$/ml | number of bone marrow cells × $10^6$/ml | number of peritoneal exudate cells × $10^6$/ml |
|---|---|---|---|---|
| Control | — | 42.8 ± 11.3[b] | 18.0 ± 2.3 | 3.8 ± 0.1[b] |
| Control | + | 28.8 ± 1.8 | 14.8 ± 4.2 | 2.4 ± 0.2 |
| RA-10 | + | 36.6 ± 7.6[b] | 15.2 ± 3.8 | 2.8 ± 0.2 |
| RA-50 | + | 41.2 ± 14.4[b] | 15.5 ± 3.2 | 2.6 ± 0.3 |
| RP-10 | + | 35.6 ± 3.8[b] | 15.0 ± 4.0 | 2.2 ± 0.1 |
| RP-50 | + | 37.6 ± 5.1[b] | 15.3 ± 2.8 | 2.4 ± 0.2 |

[b]There is a significant difference of 1% critical rate between the groups to which 5-FU was administered and the control group.

As can be seen from Table 4, the number of leukocytes were significantly improved by feeding the nutritive composition of the present invention. The number of bone marrow cells also showed the tendency of improvement. The improving effect of the nutritive composition of the present invention on the decrease in the number of leukocytes due to the administration of 5-FU was confirmed.

5) Effect on the resistivity against bacterial infection

Resistivity against primary infection was examined by infection of the living bacteria of Listeria monocytogenes (L.m.) EGD strain in mice on the 10th day after the commencement of feeding of the nutritive composition of the present invention, followed by checking the mortality rate and the number of bacteria found in the organs. When $7.25 \times 10^5$ of L.m. were inoculated into the peritoneal cavities of mice, all the mice in the control group to which 5-FU was not administered survived 14 days, whereas all the mice in the control group to which 5-FU was administered were dead. In contrast, in the retinoid administered groups, the group to which retinoic acid was administered showed that all the mice survived, while the survival rate of the group RP-10 was 20% and that of the group RP-50 was 40%. Furthermore, the number of bacteria in the spleen was examined as follows. $1 \times 10^5$ of L.m. were first injected into veins of mice, and the spleen was removed two days after the administration and homogenized, followed by dilution with sterilized saline and spread on trypticase soy agar plate. After cultivating it for 20 hours, the number of colonies were counted to calculate the number of living bacteria in spleen.

Table 5 shows the mortality rates and the number of living bacteria in the organs.

TABLE 5

Mortality rates and the number of bacteria in organs of L.m.-inoculated mice

| Number of L.m. administered to mice Feeding | 5-FU | $1.25 \times 10^5$ Mortality rate | $7.25 \times 10^5$ Mortality rate | $1 \times 10^5$ number of bacteria in organ |
|---|---|---|---|---|
| Control | — | 0/5 | 0/5 | 100 |
| Control | + | 0/5 | 5/5 | 465 |
| RA-10 | + | 0/5 | 0/5 | 174 |
| RA-50 | + | 0/5 | 0/5 | 29 |
| RP-10 | + | 0/5 | 4/5 | 387 |
| RP-50 | + | 0/5 | 3/5 | 379 |

*The number of living bacteria in organ was shown in the relative value to 100 for the control group to which 5-FU was not administered.

A significant life lengthening effect was observed in the groups to which retinoid compounds were administered. Also, the number of bacteria in organs of these groups were suppressed as compared to the groups to which 5-FU was administered, particularly that of RA-50 group was suppressed as compared even to the groups to which no 5-FU was administered. These results indicate the enhanced antibacterial activity of the spleen.

Through these experiments, the nutritive composition of the present invention was confirmed to have a nutritional effect and exhibit an immunoenhancement activity, and have preventive and therapeutic effects on the infectious diseases arising from the immunosuppression induced by medication of anticancer drugs.

By the administration of the nutritive composition of the present invention to the patients, immunosuppression induced by the administration of anticancer drugs can be prevented, and ultimately, the infectious diseases arising from said immunosuppression can be prevented and the therapeutic effect on the patients can be enhanced.

Obviously, numerous modifications and variations of the present invention are possible in light of the above teachings. It is therefore to be understood that within the scope of the appended claims, the invention may be practiced other than as specifically described herein.

What is claimed is:

1. A method for inhibiting immunosuppression in a patient which has been induced by the administration of anticancer drugs which comprises administering to said patient an immunosuppressing-inhibiting amount of a nutritive composition comprising proteins, carbohydrates, lipids, vitamins and minerals, having the following analysis, in a 400 ml aqueous solution:

| Protein | 20 g |
|---|---|
| Fat | 15 g |
| Carbohydrate | 59 g |
| Ashes | 3.2 g |
| Calcium | 440 mg |
| Iron | 5 mg |
| Vitamin C | 10.2 mg |
| Vitamin $B_1$ | 0.5 mg |
| Vitamin $B_2$ | 0.8 mg |
| Vitamin $B_6$ | 1.0 mg |
| Vitamin $B_{12}$ | 0.68 mg |
| Vitamin D | 100 IU |
| Vitamin E | 3.4 IU |
| Nicotinamide | 4.5 mg |
| Ca pantothenate | 3.4 mg |
| Folic acid | 90 μg |

-continued

| Retinoid Compound | 5 mg. |
| --- | --- |

2. The method according to claim 1, wherein said retinoid compound is one or more compounds selected from the group consisting of retinol, retinal, retinoic acid, 3-dehydroretinol, 3-dehydroretinal, 3-dehydroretinoic acid, and esters thereof.

3. The method according to claim 1, wherein said protein is selected from the group consisting of egg proteins, milk proteins, soybean proteins, fish proteins, meat proteins, and their enzymatic hydrolysates, peptide mixtures, and amino acid mixtures.

4. The method according to claim 1, wherein said lipid is selected from the group consisting of soybean oil, corn oil, safflower oil, fish oil, milk fat, and medium chain triglycerides.

5. The method according to claim 1, wherein said carbohydrate is selected from the group consisting of starch, dextrin, starch hydrolysates, dextrin hydrolysates, monosaccharides, and disaccharides.

6. The method according to claim 1, wherein from 200 to 500 grams of said nutritive composition are administered to said patient per day.

7. The method according to claim 2, wherein said retinoid compound is retinoic acid or retinoyl palmitate.

* * * * *